United States Patent
Agrawal et al.

(10) Patent No.: US 11,556,174 B1
(45) Date of Patent: Jan. 17, 2023

(54) MONITORING SYSTEM HAVING CONTEXTUAL GAZE-DETECTION-BASED SELECTION/TRIGGERING OF CAREGIVER FUNCTIONS

(71) Applicant: MOTOROLA MOBILITY LLC, Wilmington, DE (US)

(72) Inventors: Amit Kumar Agrawal, Bangalore (IN); Rahul Bharat Desai, Hoffman Estates, IL (US)

(73) Assignee: Motorola Mobility LLC, Chicago, IL (US)

(*) Notice: Subject to any disclaimer, the term of this patent is extended or adjusted under 35 U.S.C. 154(b) by 0 days.

(21) Appl. No.: 17/708,837

(22) Filed: Mar. 30, 2022

(51) Int. Cl.
| | |
|---|---|
| *G06F 3/01* | (2006.01) |
| *G16H 80/00* | (2018.01) |
| *G06V 10/25* | (2022.01) |
| *A61B 3/113* | (2006.01) |
| *G06F 16/532* | (2019.01) |
| *G03B 21/12* | (2006.01) |

(52) U.S. Cl.
CPC ............. *G06F 3/013* (2013.01); *A61B 3/113* (2013.01); *G03B 21/12* (2013.01); *G06F 16/532* (2019.01); *G06V 10/25* (2022.01); *G16H 80/00* (2018.01)

(58) Field of Classification Search
CPC ....... G06F 3/013; G06F 16/532; A61B 3/113; G03B 21/12; G06V 10/25; G16H 80/00
See application file for complete search history.

(56) References Cited

U.S. PATENT DOCUMENTS

| | | | | |
|---|---|---|---|---|
| 2010/0092929 | A1* | 4/2010 | Hallowell | G16H 50/30 434/167 |
| 2014/0253876 | A1* | 9/2014 | Klin | G16H 50/30 351/210 |
| 2015/0282705 | A1* | 10/2015 | Avital | A61B 5/163 600/301 |
| 2016/0262613 | A1* | 9/2016 | Klin | A61B 5/167 |
| 2017/0242481 | A1* | 8/2017 | Lu | G06F 3/013 |

* cited by examiner

*Primary Examiner* — Abhishek Sarma
(74) *Attorney, Agent, or Firm* — Isidore PLLC

(57) ABSTRACT

A monitoring system incorporates, and method and computer program product provide a contextual gaze detection based user selection for prompting caregiver actions by a person with ambulatory and communication deficits or limitations. A controller of the monitoring system receives receiving at least one image stream from a camera system comprising at least one image capturing device. The camera system captures a first image stream that encompasses eyes of a person and a second image stream that at least partially encompasses surrounding object(s) and surface(s) viewable by the person. The controller determines an eye gaze direction of the person and a region of interest (ROI) aligned with the eye gaze direction. The controller identifies an object and associated caregiver action contained within the ROI. The controller communicates a notification to an output device, which presents to a second person, an indication of interest by the person in the caregiver action.

20 Claims, 9 Drawing Sheets

MONITORING SYSTEM HAVING CONTEXTUAL GAZE-DETECTION-BASED SELECTION/TRIGGERING OF CAREGIVER FUNCTIONS

BACKGROUND

1. Technical Field

The present disclosure relates generally to camera-based monitoring systems that can monitor a person of interest, and more particular to camera-based monitoring systems that detect eye gaze direction of the person.

2. Description of the Related Art

Certain people who are unable to take care of themselves, such as infants, the sick, and those with ambulatory and communication deficits, require regular attention for their safety and/or well-being. A caregiver, such as a parent for an infant, who is responsible for the person is often removed from the person and rely on monitoring systems that allow the caregiver to attend to other activities while being mindful of the person being monitored and/or cared for. The monitoring systems detect at least audio and in some instances video, which are conveyed to the remote caregiver. Although use of the monitoring system allows the caregiver to move away from the cared for person, the monitoring system does not serve the needs of the cared for person nor does the monitoring system handle determining when such service is required. The caregiver has to continually assess the state of the cared-for person by paying attention to the output being locally provided of the audio and/or video captured by the remote monitoring system. If attending to other activities, the caregiver cannot scrutinize the video to understand the nuances of the state of the cared-for person, and the received output does not provide information about objects of interest to and/or objects and images viewable by the cared-for person.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1:
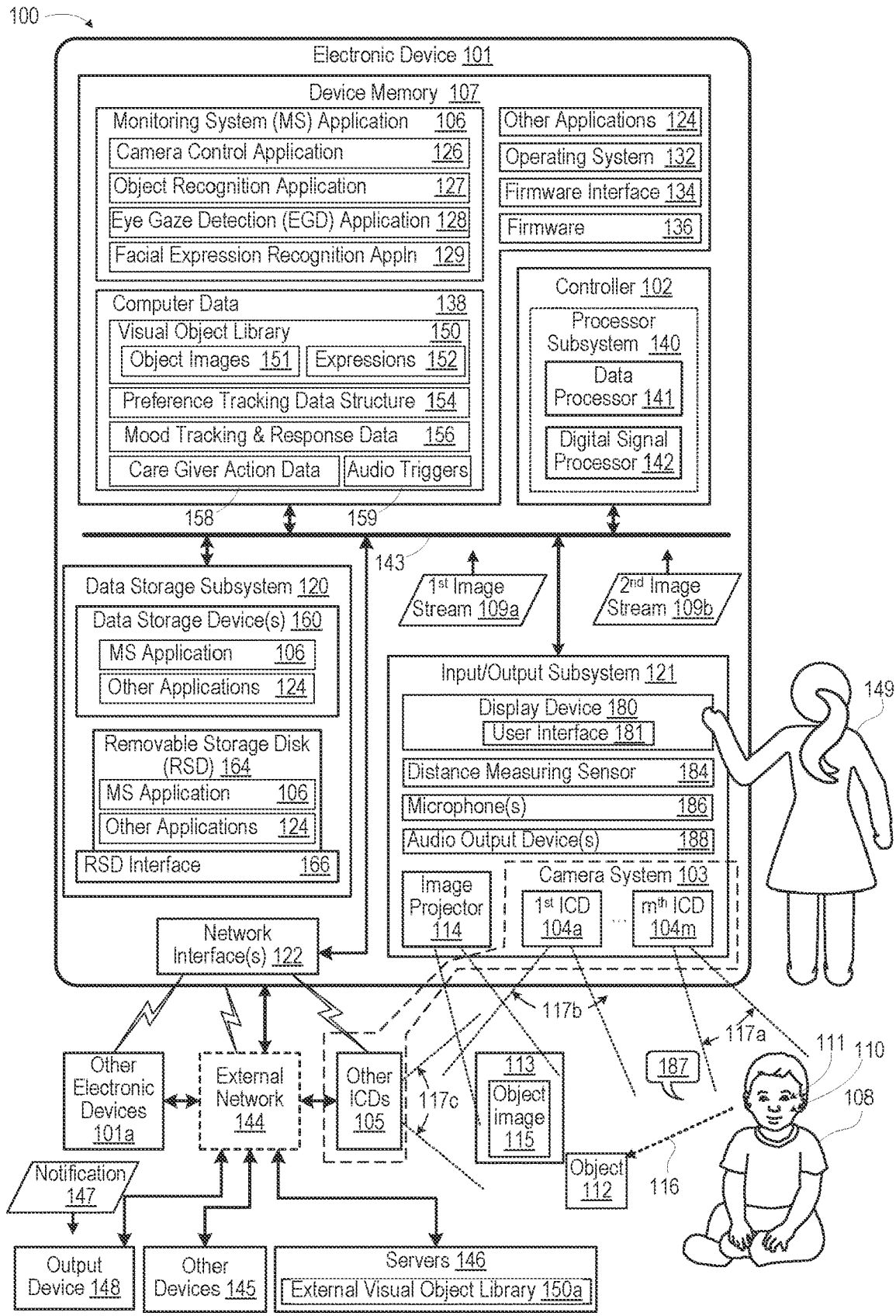
FIG. 1 depicts a functional block diagram of a monitoring system having an electronic device that detects eye-gaze direction of a person and learns about and responds to objects of subjective interest to the person, in part based on eye-gaze direction and duration, according to one or more embodiments.

According to an aspect of the present disclosure, a monitoring system incorporates a method and a computer program product that provide a gaze-detection-based user selection enabling visual selection of caregiver actions by a person with ambulatory and communication deficits or limitations. The monitoring system has a camera system including at least one image capturing device and which captures a first image stream portion that encompasses eyes of a first person of interest and a second image stream portion that at least partially encompasses one or more surrounding objects and surfaces viewable by the first person. A memory of the monitoring system stores an eye gaze detection (EGD) application. A controller of the monitoring system is communicatively coupled to the camera system and the memory. The controller executes code of the EGD application to determine an eye gaze direction of the first person. The controller determines a first region of interest (ROI) that is aligned with the eye gaze direction. The controller identifies a first object contained within the first ROI and that aligns with the eye gaze direction. The controller identifies when the first object is associated with a caregiver action. The controller communicates a notification to an output device, which presents to a second person, an indication of interest by the first person in the caregiver action. In one or more embodiments, the controller wirelessly communicates the notification.

In the following detailed description of exemplary embodiments of the disclosure, specific exemplary embodiments in which the various aspects of the disclosure may be practiced are described in sufficient detail to enable those skilled in the art to practice the invention, and it is to be understood that other embodiments may be utilized and that logical, architectural, programmatic, mechanical, electrical, and other changes may be made without departing from the spirit or scope of the present disclosure. The following detailed description is, therefore, not to be taken in a limiting sense, and the scope of the present disclosure is defined by the appended claims and equivalents thereof. Within the descriptions of the different views of the figures, similar elements are provided similar names and reference numerals as those of the previous figure(s). The specific numerals assigned to the elements are provided solely to aid in the description and are not meant to imply any limitations (structural or functional or otherwise) on the described embodiment. It will be appreciated that for simplicity and clarity of illustration, elements illustrated in the figures have not necessarily been drawn to scale. For example, the dimensions of some of the elements are exaggerated relative to other elements.

It is understood that the use of specific component, device and/or parameter names, such as those of the executing utility, logic, and/or firmware described herein, are for example only and not meant to imply any limitations on the described embodiments. The embodiments may thus be described with different nomenclature and/or terminology utilized to describe the components, devices, parameters, methods and/or functions herein, without limitation. References to any specific protocol or proprietary name in describing one or more elements, features or concepts of the embodiments are provided solely as examples of one implementation, and such references do not limit the extension of the claimed embodiments to embodiments in which different element, feature, protocol, or concept names are utilized. Thus, each term utilized herein is to be given its broadest interpretation given the context in which that term is utilized.

As further described below, implementation of the functional features of the disclosure described herein is provided within processing devices and/or structures and can involve use of a combination of hardware, firmware, as well as several software-level constructs (e.g., program code and/or program instructions and/or pseudo-code) that execute to provide a specific utility for the device or a specific functional logic. The presented figures illustrate both hardware components and software and/or logic components.

Those of ordinary skill in the art will appreciate that the hardware components and basic configurations depicted in the figures may vary. The illustrative components are not intended to be exhaustive, but rather are representative to highlight essential components that are utilized to implement aspects of the described embodiments. For example, other devices/components may be used in addition to or in place of the hardware and/or firmware depicted. The depicted example is not meant to imply architectural or other limitations with respect to the presently described embodiments and/or the general invention. The description of the illustrative embodiments can be read in conjunction with the accompanying figures. Embodiments incorporating teachings of the present disclosure are shown and described with respect to the figures presented herein.

FIG. 1 is a functional block diagram of an example of monitoring system 100 that includes at least one electronic device 101 in an operating environment within which the features of the present disclosure are advantageously implemented. In particular, controller 102 of electronic device 101 is communicatively coupled to camera system 103 having one or more image capturing devices (ICDs) 104a-104m. Camera system 103 can also include other detached ICDs 105 that are external to electronic device 101. Controller executes monitoring system application 106 in device memory 107 to configure electronic device 101 as a monitoring system for first person 108 of interest, such as an infant, a small child, or an adult with ambulatory and communication deficits. Camera system 103 captures first image stream 109a that encompasses face 110 including eyes 111 of first person 108 of interest and second image stream 109b that at least partially encompasses one or more surrounding tangible objects 112 and surfaces 113 viewable by first person 108. Image projector 114 of electronic device 101 (or provided as a second device of monitoring system) may project object images 115 on surfaces 113 that are within the field of view of (i.e., visible to) first person 108. First person 108 demonstrates interest in tangible objects 112 and/or object images 115 at least in part by the person's eye gaze direction 116. In one or more embodiments, camera system 103 includes more than one ICD 104a-104m and/or detached ICDs 105 and thus is a multi-camera camera system. In an example, mth ICD 104m has a first field of view (FOV) 117a configured to encompass first image stream 109a. First ICD 104a has second FOV 117b configured to encompass second image stream 109b.

In one or more embodiments, camera system 103 includes one ICD 104a and is a single camera system. In an example, one detached ICD 105 has third FOV 117c configurable to encompass both first image stream 109a and second image stream 109b, simultaneously viewing face 110 and eyes 111 of person 108 as well as object 112 and/or object image 115. In another example, detached ICD 105 has configurable third FOV 117c configurable in a first direction to encompass first image stream 109a and in a second direction to encompass second image stream 109b, alternating between viewing face 110 and eyes 111 of person 108 and then object 112 and/or object image 115 located in the eye gaze direction of person 108. In one or more embodiments, the ability to configure detached ICD 105 can be enabled with use of a gimbal that enables rotation of the camera lens between at least the first and second directions.

Electronic device 101 can be one of a host of different types of devices, including but not limited to, an infant monitoring system, a mobile cellular phone, satellite phone, or smart-phone, a laptop, a net-book, an ultra-book, a networked smart watch, networked sports/exercise watch, and/or a tablet computing device or similar device. As more completed presented within communication device 200 of FIG. 2, described hereafter, electronic device 101 can also be a device supporting wireless communication. In these implementations, electronic device 101 can be utilized as, and also be referred to as, a system, device, subscriber unit, subscriber station, mobile station (MS), mobile, mobile device, remote station, remote terminal, user terminal, terminal, user agent, user device, a Session Initiation Protocol (SIP) phone, a wireless local loop (WLL) station, a personal digital assistant (PDA), computer workstation, a handheld device having wireless connection capability, a computing device, or other processing devices connected to a wireless modem. Most importantly, it is appreciated that the features described herein can be implemented with a display device of various other types of electronic devices that are not necessarily a communication device. The specific presentation or description herein of a mobile communication device in addition to a data processing system as different examples of electronic device 101 are for example only, and not intended to be limiting on the disclosure.

Referring now to the specific component makeup and the associated functionality of the presented components. In one or more embodiments, in addition to device memory 107, electronic device 101 includes data storage subsystem 120, input/output (I/O) subsystem 121, and network interface 122, each of which is managed by controller 102. Device memory 107 includes program code for applications, such as monitoring system application 106 and other applications 124. In one or more embodiments, monitoring system application 106 is a suite of applications, utilities, components, or modules that configure electronic device 101 to monitor first person 108. In an example, monitoring system application 106 includes camera control application 126, object recognition application 127, eye gaze detection application 128, and facial expression recognition application 129. Device memory 107 further includes operating system (OS) 132, firmware interface 134, such as basic input/output system (BIOS) or Uniform Extensible Firmware Interface (UEFI), and firmware 136. Device memory 107 stores computer data 138 that is used by monitoring system application 106.

Controller 102 includes processor subsystem 140, which executes program code to provide operating functionality of electronic device 101. Controller 102 manages, and in some instances directly controls, the various functions and/or operations of electronic device 101. These functions and/or operations include, but are not limited to including, application data processing, communication with second communication devices, navigation tasks, image processing, and signal processing. In one or more alternate embodiments, electronic device 101 may use hardware component equivalents for application data processing and signal processing. For example, electronic device 101 may use special purpose hardware, dedicated processors, general purpose computers, microprocessor-based computers, micro-controllers, optical computers, analog computers, dedicated processors and/or dedicated hard-wired logic.

The software and/or firmware modules executed by processor subsystem 140 have varying functionality when their corresponding program code is executed by data processor (s) 141 or secondary processing devices within electronic device 101 such as digital signal processor 142. Processor subsystem 140 can include other processors that are communicatively coupled internally or externally to data processor 141. Data processor 141 is communicatively coupled, via system interlink 143, to device memory 107, data storage subsystem 120, and network interface 122. System interlink 143 represents internal components that facilitate internal communication by way of one or more shared or dedicated internal communication links, such as internal serial or parallel buses. As utilized herein, the term "communicatively coupled" means that information signals are transmissible through various interconnections, including wired and/or wireless links, between the components. The interconnections between the components can be direct interconnections that include conductive transmission media or may be indirect interconnections that include one or more intermediate electrical components. Although certain direct interconnections (system interlink 143) are illustrated in FIG. 1, it is to be understood that more, fewer, or different interconnections may be present in other embodiments.

Network interface 122 enables electronic device 101 to connect (via wireless or wired connection) to external network 144 and directly/indirectly to other devices 145. Network 144 provides connection to and can include one or more network servers 146 and can provide connection to other devices 145. Electronic device 101 is thus able to connect with servers 146 and other devices 145 to share and/or download application data that can be utilized to implement features of the disclosure. In an example, servers 146 may contain external visual object library 150a. Monitoring system 100 may include more than one electronic devices 101 that either are communicatively coupled to cooperate in detection and response to cover additional portions of a room or a different room. Electronic device 101 may communicate notifications 147 to output device 148 used by second person 149. Second person 149 may be a human being, a robot, a support machine, or a customer service dispatch system. In one or more embodiments, network interface 122 of communication device 200 includes a network connection such as an Ethernet receptacle that connected by a network cable to a wired area network. Network interface 122 can support one or more network communication protocols such as a local area network (LAN), a campus area network (CAN), a metropolitan area network (MAN), or a wide area network (WAN).

Processor subsystem 140 of controller 102 can execute program code of monitoring system application 106 to configure electronic device 101 to perform specific functions that use or create computer data 138. In an example, computer data 138 includes visual object library 150 having stored object images 151 and facial expressions 152. Computer data 138 also may include preference tracking data structure 154, mood tracking and response (MTR) data structure 156, caregiver action data 158, and audio trigger data 159. These various data are referenced and updated by monitoring system application 106.

Data storage subsystem 120 of electronic device 101 includes data storage device(s) 160. Controller 102 is communicatively connected, via system interlink 143, to data storage device(s) 160. Data storage subsystem 120 provides applications, program code, and stored data on nonvolatile storage that is accessible by controller 102. For example, data storage subsystem 120 can provide a selection of applications and computer data, such as monitoring system application 106 and other application(s) 124. These applications can be loaded into device memory 107 for execution by controller 102. In one or more embodiments, data storage device(s) 160 can include hard disk drives (HDDs), optical disk drives, and/or solid-state drives (SSDs), etc. Data storage subsystem 120 of electronic device 101 can include removable storage device(s) (RSD(s)) 164, which is received in RSD interface 166. Controller 102 is communicatively connected to RSD 164, via system interlink 143 and RSD interface 166. In one or more embodiments, RSD 164 is a non-transitory computer program product or computer readable storage device. Controller 102 can access RSD 164 or data storage device(s) 160 to provision electronic device 101 with program code, such as code for monitoring system application 106 and other application(s) 124, and with computer data 138 such as visual object library 150.

In addition to ICDs 104a-104m and image projector 114, I/O subsystem 121 includes display device 180 that presents user interface 181 for use by second person 149 when in the room with monitoring system 100. Second person 149 may also remotely control or view output from monitoring system 100 via output device 148. In one or more embodiments, ICDs 104a-104m provide three-dimensional data or are augmented by distance measuring sensor 184 to assist in determining relative locations of first person 108, objects 112 and surfaces 113. Controller 102 can then use eye gaze direction 116 of first person 108 to identify regions of interest (ROI) to first person 108. I/O subsystem 121 includes microphone(s) 186 that can be used to receive audio input 187 from first person 108, such as sounds of crying, giggling, laughing, and talking, which, in addition to or in conjunction with facial expressions, indicate a mood of first person 108. I/O subsystem 121 includes audio output device(s) 188 that may produce soothing sounds or communication from other devices 145.

In one aspect of the present disclosure, electronic device 101 includes camera system 103, which includes at least one image capturing device (104a-104m, 105) and which captures first image stream 109a that encompasses eyes 111 of first person 108 of interest and second image stream 109b that at least partially encompasses one or more surrounding objects 112 and surfaces 113 viewable by first person 108. Device memory 107 stores EGD application 128. Controller 102 is communicatively coupled to camera system 103 and device memory 107. Controller 102 triggers EGD application 128 to determine eye gaze direction 116 of first person 108. Controller 102 determines a first ROI that is aligned with eye gaze direction 116. Controller 102 identifies first object 112 contained within the first ROI. Controller 102 identifies an association of a caregiver action with first object 112. Controller 102 communicates notification 147 to output device 148, which presents to second person 149, an indication of interest by first person 108 in the caregiver action.

Figure 2:
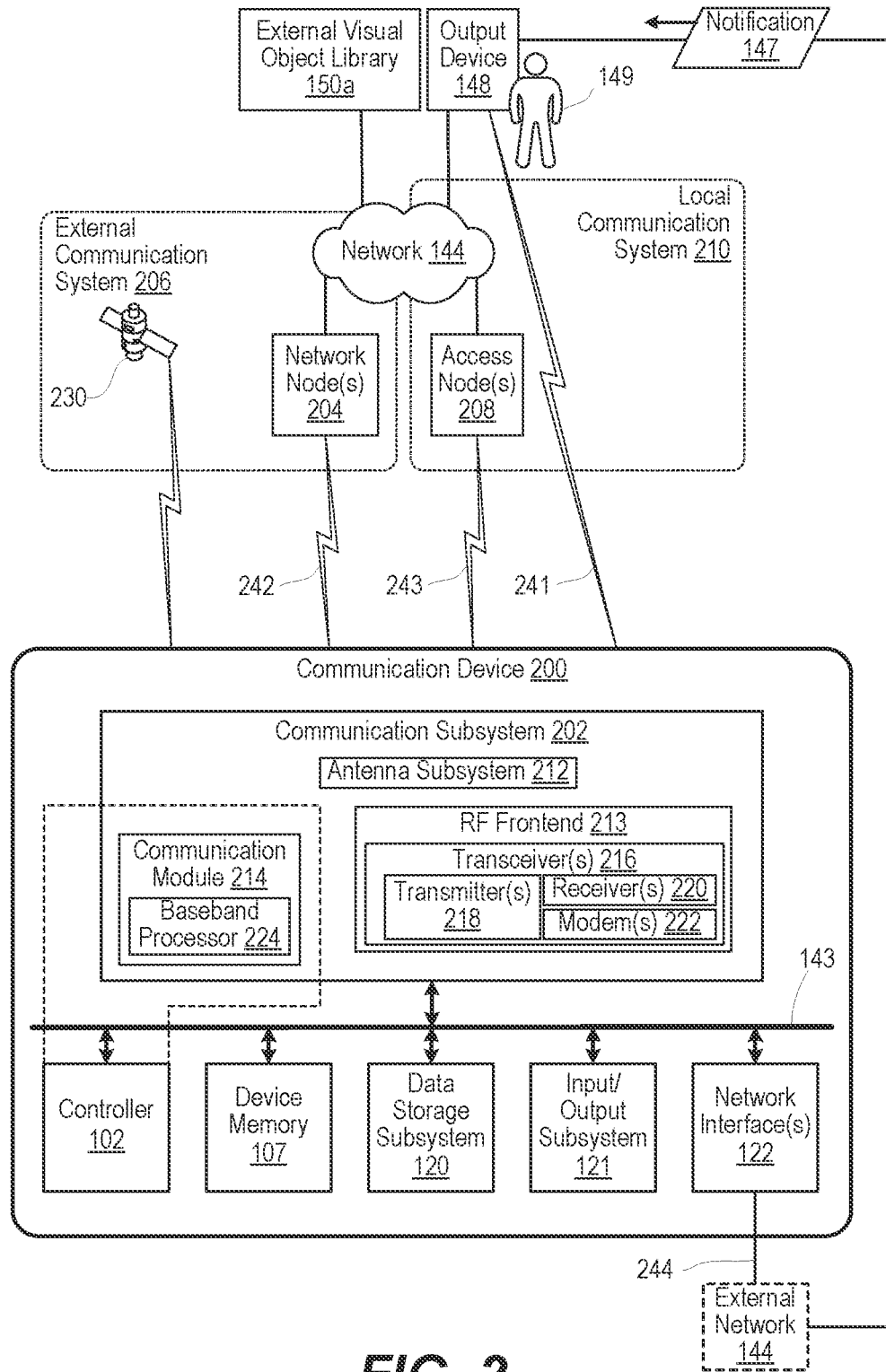
FIG. 2 depicts a functional block diagram of a monitoring system having a communication device that performs learning and notification functions based on detected eye-gaze direction of a person in an operating environment within which the features of the present disclosure are advantageously implemented, according to one or more embodiments.

FIG. 2 is a functional block diagram of communication device 200 in an operating environment within which the features of the present disclosure are advantageously implemented. Communication device 200 is an implementation of electronic device 101 (FIG. 1), including controller 102, device memory 107, data storage subsystem 120, I/O subsystem 121, and network interface(s) 122. Communication device 200 further includes communication subsystem 202 for communicating, using a cellular connection, with network node(s) 204 of external communication system 206 and for communicating, using a wireless connection, with access node(s) 208 of local communication system 210. Communication subsystem 202 includes antenna subsystem 212. Communication subsystem 202 includes radio frequency (RF) front end 213 and communication module 214. RF front end 213 includes transceiver(s) 216, which includes transmitter(s) 218 and receiver(s) 220. RF front end 213 further includes modem(s) 222. Communication module 214 of communication subsystem 202 includes baseband processor 224 that communicates with controller 102 and RF front end 213. Baseband processor 224 operates in a baseband frequency range to encode data for transmission and decode received data, according to a communication protocol. Modem(s) 222 modulate baseband encoded data from communication module 214 onto a carrier signal to provide a transmit signal that is amplified by transmitter(s) 218. Modem(s) 222 demodulates each signal received from external communication subsystem 202 using by antenna subsystem 212. The received signal is amplified and filtered by receiver(s) 220, which demodulate received encoded data from a received carrier signal.

In one or more embodiments, controller 102, via communication subsystem 202, performs multiple types of cellular OTA or wireless communication with local communication system 210. Communication subsystem 202 can communicate via an over-the-air (OTA) connection 241 with output device 148 used by second person 149 ("caregiver"). In an example, OTA connection 241 is a peer-to-peer connection, Bluetooth connection, or other personal access network (PAN) connection. In another example, output device 148 is as a smart watch or a wireless headset. In an additional example, output device 148 is a head worn device such as smart glasses, a helmet mounted display (HMD), or visors that present a virtual reality (VR), extended reality (XR), or augmented reality (AR) service. In one or more embodiments, communication subsystem 202 communicates with one or more locally networked devices via a wireless local area network (WLAN) link provided by access node(s) 208. In one or more embodiments, access node(s) 208 supports communication using one or more IEEE 802.11 WLAN protocols. Access node(s) 208 is connected to a wide area network such as the Internet. In one or more embodiments, communication subsystem 202 communicates with GPS satellites 230 to obtain geospatial location information. communication subsystem 202 communicates via network node(s) 204 or access node(s) 204 and external network 144 with external visual object library 150a.

Controller 102 communicates notification 147 to output device 148 for presenting to second person 149. In one or more embodiments, controller communicates with output device 148 via OTA connection 241 between communication subsystem 202 and output device 148. In one or more embodiments, controller communicates with output device 148 via cellular connection 242 between communication subsystem 202 and base node 204. In one or more embodiments, controller communicates with output device 148 via wireless connection 243 between communication subsystem 202 and access node 208. In one or more embodiments, controller communicates with output device 148 via wired connection 244 between network interface 122 and external network 144.

Figure 3:
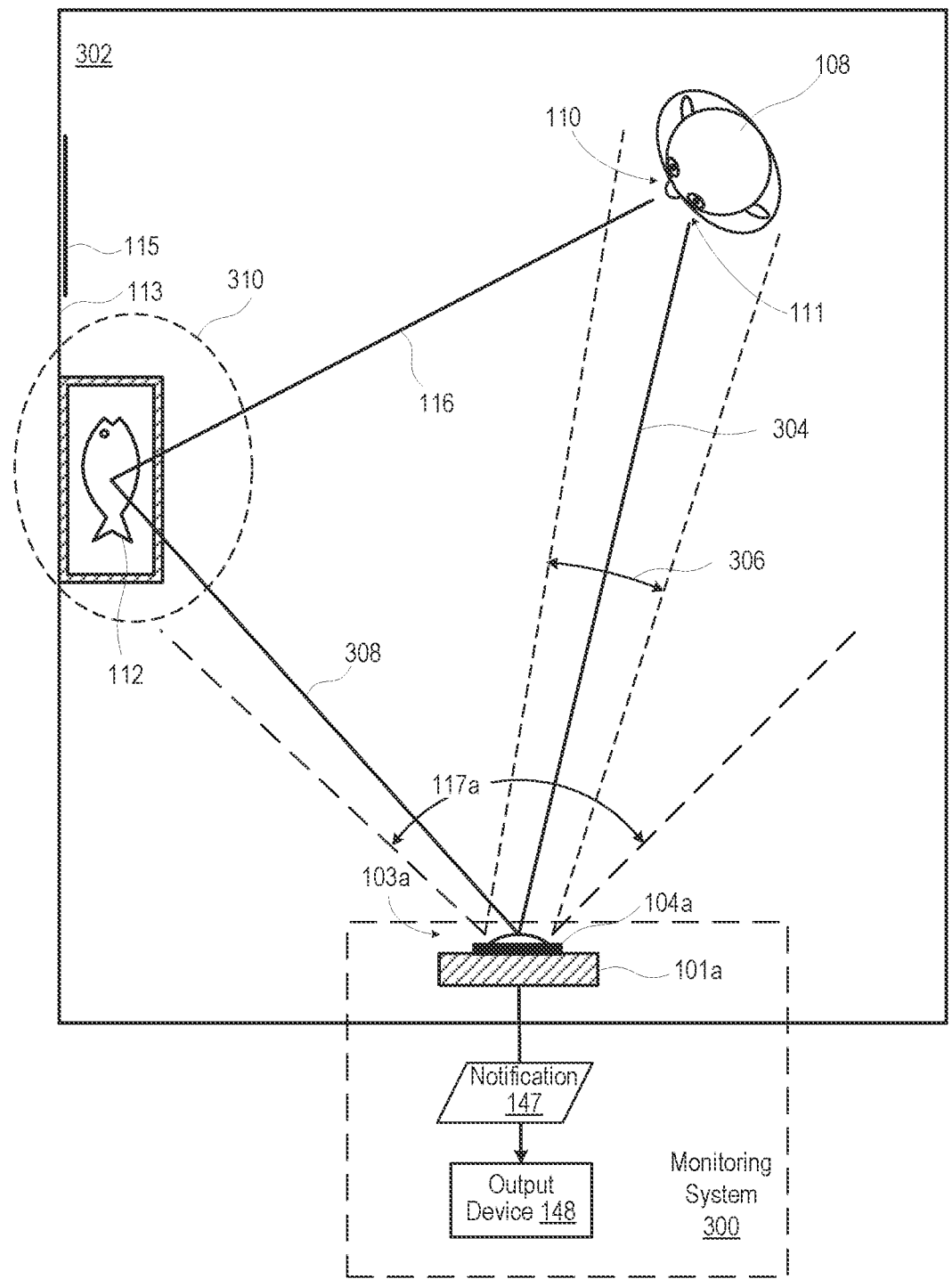
FIG. 3 is a top view diagram of a monitoring system provided by the electronic device of FIG. 1 or the communication device of FIG. 2 having a single camera system with one image capturing device (ICD) positioned to monitor a person and objects of interest to the person in a surrounding space viewable within the field of view of the single camera system, according to one or more embodiments.

FIG. 3 is a top view diagram of monitoring system 300 provided by single electronic device 101a having single camera system 103a with one ICD 104a positioned to monitor first person 108 in room 302. Monitoring system 300 includes output device 148 that is outside of room 302 and that receives notification 147. ICD 104a is positioned and controlled to have FOV 117a that simultaneously encompasses face 110 and eyes 111 of person 108 (first image stream 109a of FIG. 1) and also object 112 (second image stream 109b of FIG. 1) that is aligned with eye gaze direction 116 of person 108. For clarity, eye gaze direction 116 is depicted in two-dimension; however, electronic device 101a determines eye gaze direction 116 in three-dimensions based on determining location of first person 108 and orientation of face 110 and eyes 111 of first person 108 to ICD 104. Electronic device 101a determines direction 304 to first person 108 and distance to first person 108 to obtain location. Distance may be based on an apparent angular dimension 306 of first person 108 as viewed by ICD 104a or may be based on distance detection by distance measuring sensor 184 (FIG. 1). Electronic device 101 also determines direction 308 to location of a region of interest (ROI) 310 that is aligned with gaze direction 304. Within ROI 310, electronic device 101a identifies any objects 112 or object images 115 on surfaces 113.

Figure 4:
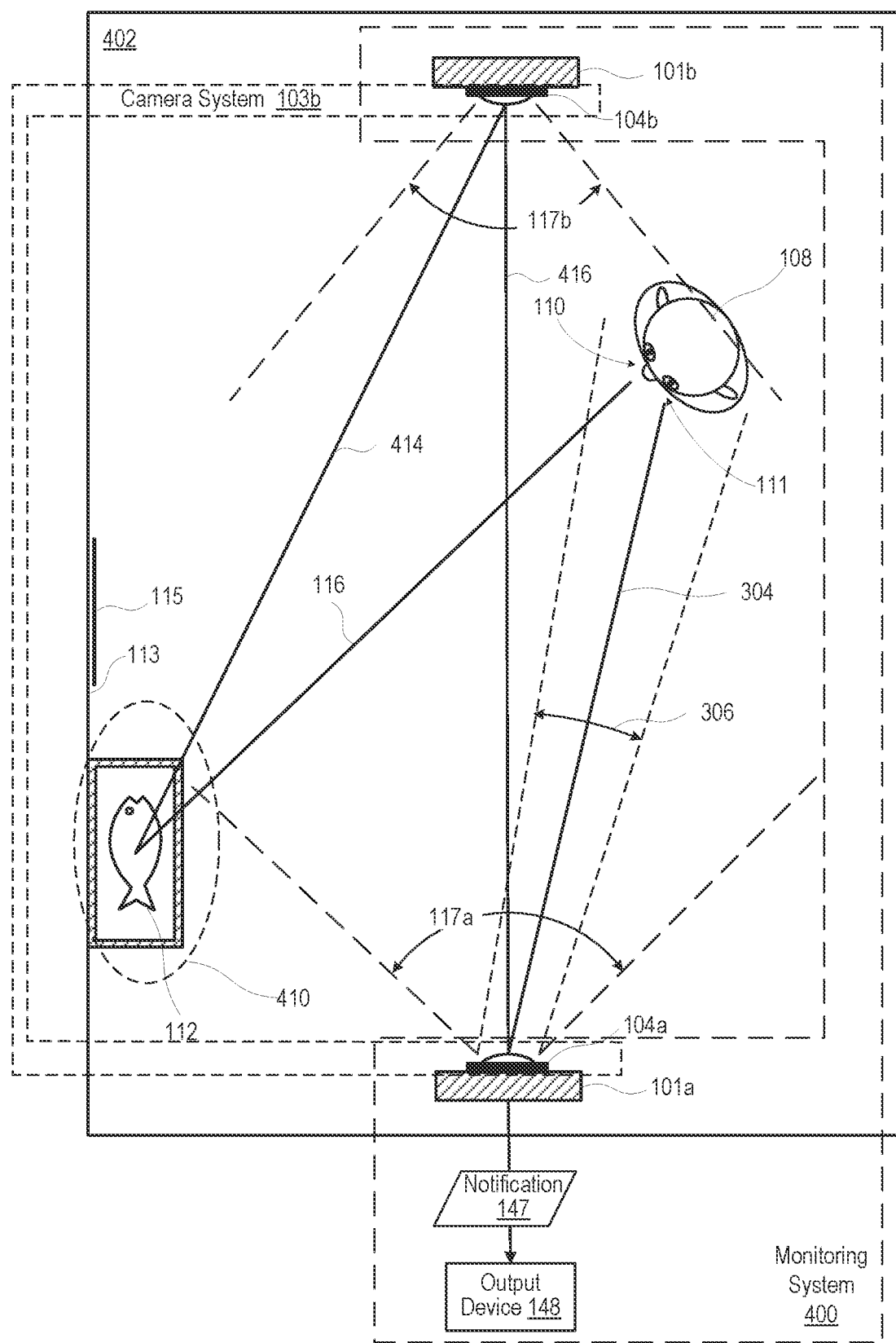
FIG. 4 is a top view diagram of a monitoring system provided by separate camera devices positioned to respectively monitor a person and objects in a surrounding space, according to one or more embodiments.

FIG. 4 is a top view diagram of monitoring system 400 having multi-camera system 103 provided in part by first electronic device 101a with first ICD 104a having FOV 117a positioned to monitor first person 108 in room 402. In particular, ICD 104a is positioned and controlled to have FOV 117 to encompasses face 110 and eyes 111 of person 108, which are presented within first image stream 109a of FIG. 1. Multi-camera system 103b is also provided in part by second electronic device 101b with second ICD 104b having FOV 117b positioned to monitor a space opposed to face of person and within which one or more objects 111 and/or object images can be found or positioned for viewing by person. The space can be in room 402, and objects and/or object images captured within FOV are presented within second image stream 109b of FIG. 1. Monitoring system 400 includes output device 148 that is located outside of room 402 and which receives and presents notification 147.

Second electronic device 101b determines direction 414 and distance from second electronic device 101b to object 112 and object image 115. Object 112 in first ROI 310 is aligned with eye gaze direction 116 of person 108. For clarity, eye gaze direction 116 is depicted in two-dimension; however, first electronic device 101a determines eye gaze direction 116 is determined and extrapolated in three-dimensions as described above. In one embodiment, a relative direction 416 and distance between first and second electronic device 101a-101b and person 108 are determined in order to enable the correct extrapolation of eye gaze direction to a region of interest captured by second ICD of second electronic device 101b. In an example, communication signals between first and second electronic device 101a-101b provide indications of direction and distance of each device. In another example, optical analysis between first and second electronic device 101a-101b may be use by controlling processor of monitoring system 400 to determine relative direction and distance. With collaboration of direction and distance information between first and second electronic device 101a-101b and based on determining location of first person 108 and orientation of face 110 and eyes 111 of first person 108 to ICD 104, monitoring system 400 determines that eye gaze direction 116 monitored by electronic device 101a is aligned with a determined first ROI 410 that can be monitored by second electronic device 101b. According to one embodiment, electronic device 101 determines direction 304 to first person 108 and distance to first person 108 to obtain location of first person 108. Electronic device 101 also determines direction 308 to location of a region of interest (ROI) 310 that is aligned with gaze direction 304. Within ROI 308, electronic device 101 identifies any objects 112 or object images 115 on surfaces 113.

Figure 5A:
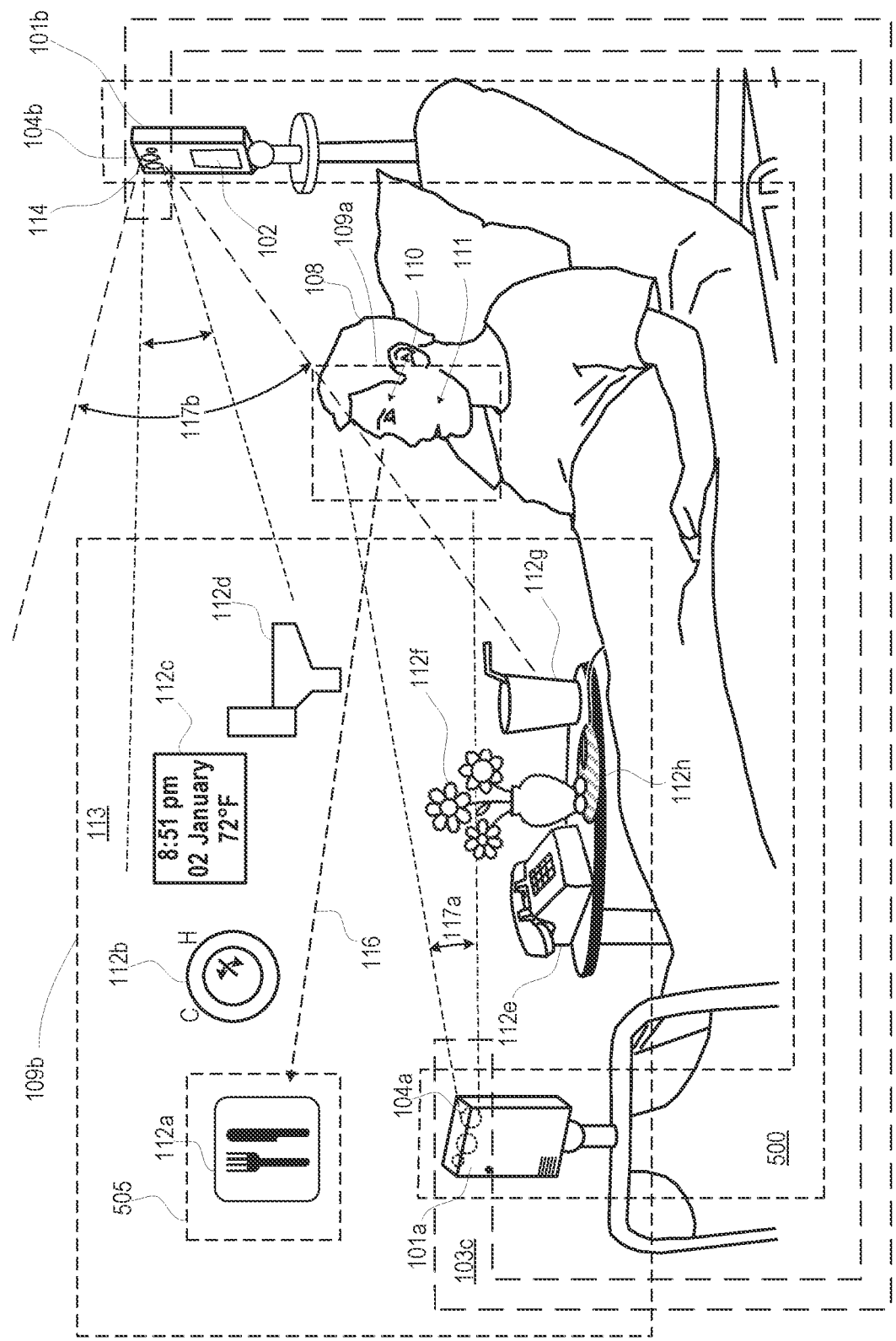
FIG. 5A is a side view of a monitoring system having electronic devices of FIG. 1 or communication devices of FIG. 2 that provide a contextual gaze-detection-based user selection for prompting caregiver actions by a person with ambulatory and communication deficits or limitations, according to one or more embodiments.

FIG. 5A is a side view of monitoring system 500 having first and second electronic devices 101a-101b that provide a contextual gaze-detection-based user selection for prompting/requesting caregiver actions by a person with ambulatory and communication deficits or limitations. First and second electronic devices 101a-101b each may include the functionality and components of electronic device 101 of FIG. 1 or communication device 200 of FIG. 2. Monitoring system 500 includes dual camera system 103c provided by respective front ICDs 104a of first electronic device 101a and front ICD 104b of second electronic device 101b. Front ICD 104a of camera system 103c has first FOV 117a that captures first image stream 109a that encompasses eyes 111 of first person 108. Front ICD 104b of camera system 103c has second FOV 117b that captures second image stream 109b that at least partially encompasses one or more surrounding objects 112a— h and surfaces 113 viewable by first person 108.

In an example, objects 112a-112d are object images 115 (FIG. 1) projected on surface 113 by image projector 114 of second electronic device 101b. First object 112a is a food symbol associated with a caregiver action for nutrition. Second object 112b is a thermostat symbol associated with a caregiver action for thermal environment regulation. Third object 112c is a time/date/temperature sign that is not associated with a caregiver action. Fourth object 112d is a toilet symbol associated with a caregiver action for hygiene. Objects 112e-112h are tangible objects. Fifth object 112e is a telephone that is associated with a caregiver action for communication. Sixth object 112f is a vase with flowers that is not associated with a caregiver action. Seventh object 112g is a drinking cup associated with a caregiver action for hydration. Eighth object 112h is a television controller associated with a caregiver action for entertainment.

Controller 102 determines eye gaze direction 116 of first person 108. Controller 102 determines a first ROI 505 that is aligned with eye gaze direction 116. Controller 102 identifies first object 112 contained within the first ROI. Controller 102 identifies an association of a caregiver action with first object 112a. Controller 102 communicates notification 147 to output device 148, which presents to second person 149 (FIG. 1), an indication of interest by first person 108 in the particular caregiver action.

In one or more embodiments, controller 102 determines when first person 108 is interested in or is selecting first object 112a by determining an uninterrupted duration of time in which eye gaze direction 116 is maintained on first ROI. In an example, a duration threshold of 3 seconds may indicate selection by first person 108. Alternatively, or in addition to, controller 102 determines when first person 108 is interested in or is selecting first object 112a by determining a frequency of glances in eye gaze direction 116 toward first ROI. In an example, eye gaze direction 116 is within first ROI 505 three times within 5 seconds. In one or more embodiments, a threshold duration of time value or a threshold frequency of glancing value is adjusted to cognitive or eye control abilities of first person 108. The adjustment may be a one-time adjustment or be a dynamic adjustment in relation to how tired first person 108 is. In one or more embodiments, controller 102 monitors eye gaze direction 116 to detect an unusual eye gaze direction 116 controller 102 determines when first person 108 is interested in or is selecting first object 112a by determining an uninterrupted duration of time in which eye gaze direction 116 is maintained on first ROI. In an example, an ROI that is near front and center of first person 108 require a longer duration or frequency of eye gaze direction 116 than ROI that require a greater turning of face 110 and/or eyes 111. In one or more embodiments, eye gaze detection by monitoring system 500 has sufficient resolution to detect encoded eye movements by first person 108 In an example, first person 108 may look such that eye gaze direction 116 passes vertical across first ROI 505 followed by passing horizontally across first ROI 505 to indicate a volitional intent to activate an automatic caregiver action associated with first ROI 505.

In one or more embodiments, monitoring system 500 recognizes, by referencing visual object library 150 (FIG. 1), one or more objects 112a-112h, including first object 112a, present in at least one FOV 117b. Controller 102 identifies an association of at least first object with one more caregiver actions that are mapped within visual object library 150 (FIG. 1). In one or more particular embodiments, network interface 122 is communicatively connected via external network 144 to external visual object library 150a (FIGS. 1-2). In response to not finding an association within local visual object library 150 (FIG. 1), controller 102 identifies an association of at least first object 112a with one more caregiver actions that are mapped within external visual object library 150a (FIGS. 1-2).

In one or more particular embodiments, the presentation of objects associated with caregiver actions is provided by image projector 114 linked to monitoring system 100. Projector can be integrated into electronic device 101 or be a separate stand-alone image projector 114 that is communicatively coupled and controlled by controller 102 of electronic device 101. In one embodiment, controller 102 recognizes, using visual object library 150 (FIG. 1), one or more tangible objects (112e-112h) that are present in at least one image stream 109b in at least one region. Controller 102 attempts to identify respective tangible object (112e-112h) of the one or more tangible objects (112e-112h) associated with each of the one or more caregiver actions. In response to determining that no caregiver actions are represented by a tangible object recognized in the at least one image stream, controller 102 identifies images of objects 112a, 112b and 112d in the visual object library that are associated with one of the caregiver actions. Controller 102 triggers image projector 114 to project images as objects 112a, 112b and 112d on surfaces 113 that are within view of person 108. In one or more embodiments, controller 102 projects, in sequence, each of different objects 112a, 112b, and 112d associated with the one or more caregiver actions on first ROI 505. Each object is projected for a period of time (e.g., 5 seconds) before being replaced by the next object. In one or more embodiments, controller 102 projects different objects 112a, 112b and 112d associated with the one or more caregiver actions at respective different regions of surface 113 within a surrounding area visible to first person 108. First person 108 is then able to select from among the presented objects by affixing his/her eye gaze on the object of interest, for the minimum threshold period (e.g., 3 seconds) in order to trigger the generation of the notification and subsequent caregiver response.

Figure 5B:
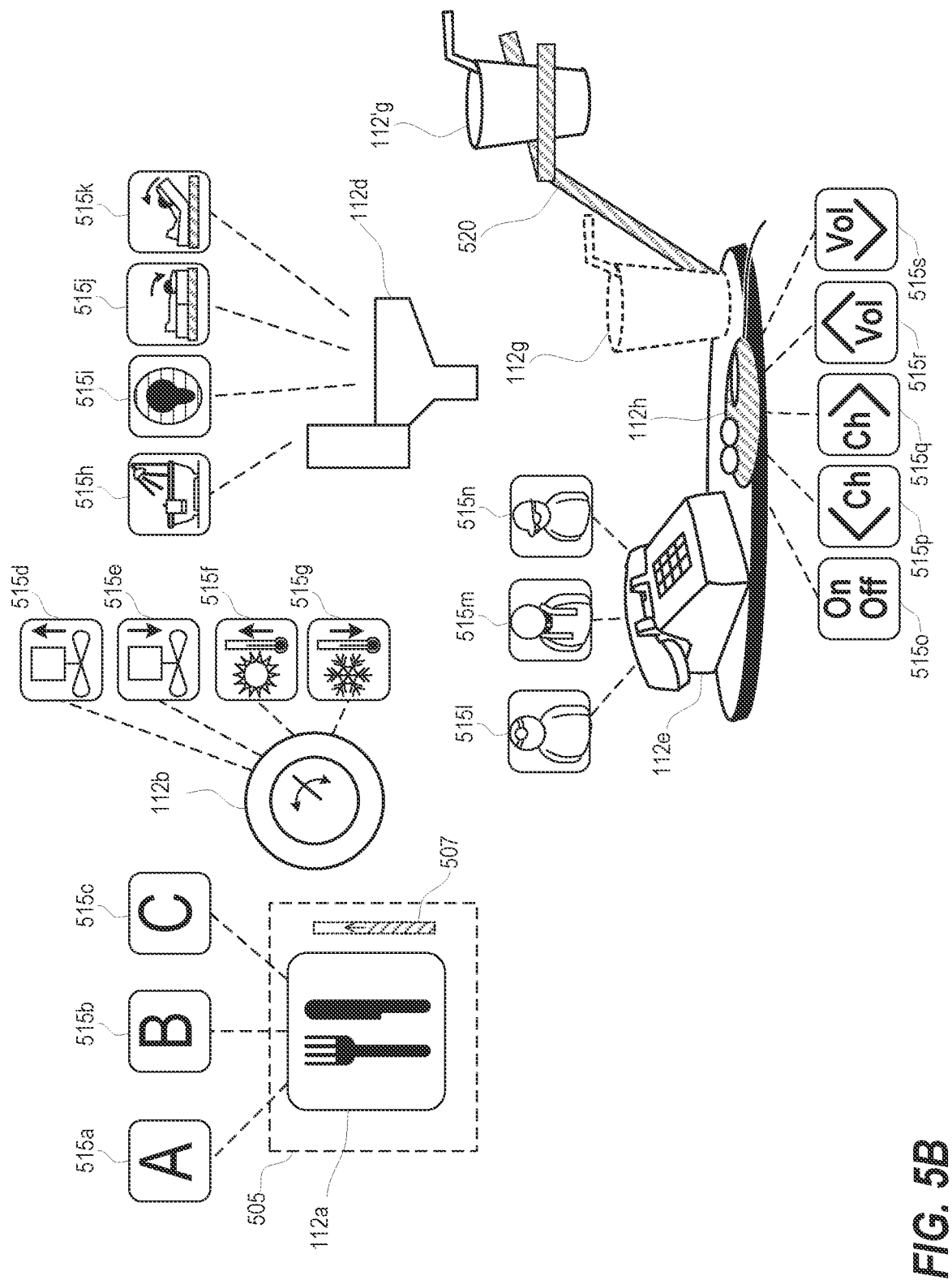
FIG. 5B is a side view of objects projected by the monitoring system of FIG. 5A in response to the contextual gaze-detection-based user selection, according to one or more embodiments.

FIG. 5B is a side view of lower tier objects 515a-515s projected by monitoring system 500 of FIG. 5A in response to the contextual gaze-detection-based user selection of one of objects 112a, 112b, 112d, 112e and 112h. In response to detecting eye gaze direction 116 (FIG. 5A) being on first ROI 505, a duration or frequency meter 507 is projected on surface 113 proximate to object 112a, indicating progress in selecting object 112a. In an example, selection of object 112a associated with the caregiver action of nutrition triggers projecting lower-tier objects 515a-515c that sequentially and/or spatially present alphanumeric characters to spell out a food menu item of interest to first person 108 (FIG. 5A). Lower-tier object 515a presents a letter "A". Lower-tier object 515b presents a letter "B". Lower-tier object 515c presents a letter "C". In another example, in response to selecting object 112b associated with the caregiver action of environmental thermal controls, monitoring system 500 (FIG. 5A) projects sequentially and/or spatially separated lower-tier objects 515d-515g. Lower-tier object 515d presents a control icon for increasing fan speed. Lower-tier object 515e presents a control icon for decreasing fan speed. Lower-tier object 515f presents a control icon for increasing thermostat temperature. Lower-tier object 515g presents a control icon for decreasing thermostat temperature. In an additional example, selection of object 112d associated with the caregiver action of hygiene triggers sequential and/or spatially separated presentation of lower-tier objects 515h-515k. Lower-tier object 515h is a bath icon. Lower-tier object 515i is a bedpan icon. Lower-tier object 515j is a raise bed icon. Lower-tier object 515k is a lower bed icon. In a further example, selection of object 112e associated with the caregiver action of communication triggers sequential and/or spatially-separated presentation of lower-tier objects 515l-515n. Lower-tier object 515l is a doctor icon. Lower-tier object 515m is a cleric icon. Lower-tier object 515n is a maintenance icon. In yet a further example, selection of object 112h associated with the caregiver action of entertainment triggers sequential and/or spatially-separated projection of lower-tier objects 515o-515s. Lower-tier object 515o is a television on/off toggle icon. Lower-tier object 515p is a channel down control icon. Lower-tier object 515q is a channel up control icon. Lower-tier object 515r is a volume down control icon. Lower-tier object 515s is a volume up control icon. In response to selection of object 112g, monitoring system 500 (FIG. 5A) triggers robotic system 520 to raise object 112g to a raised position (112'g).

Figure 6:
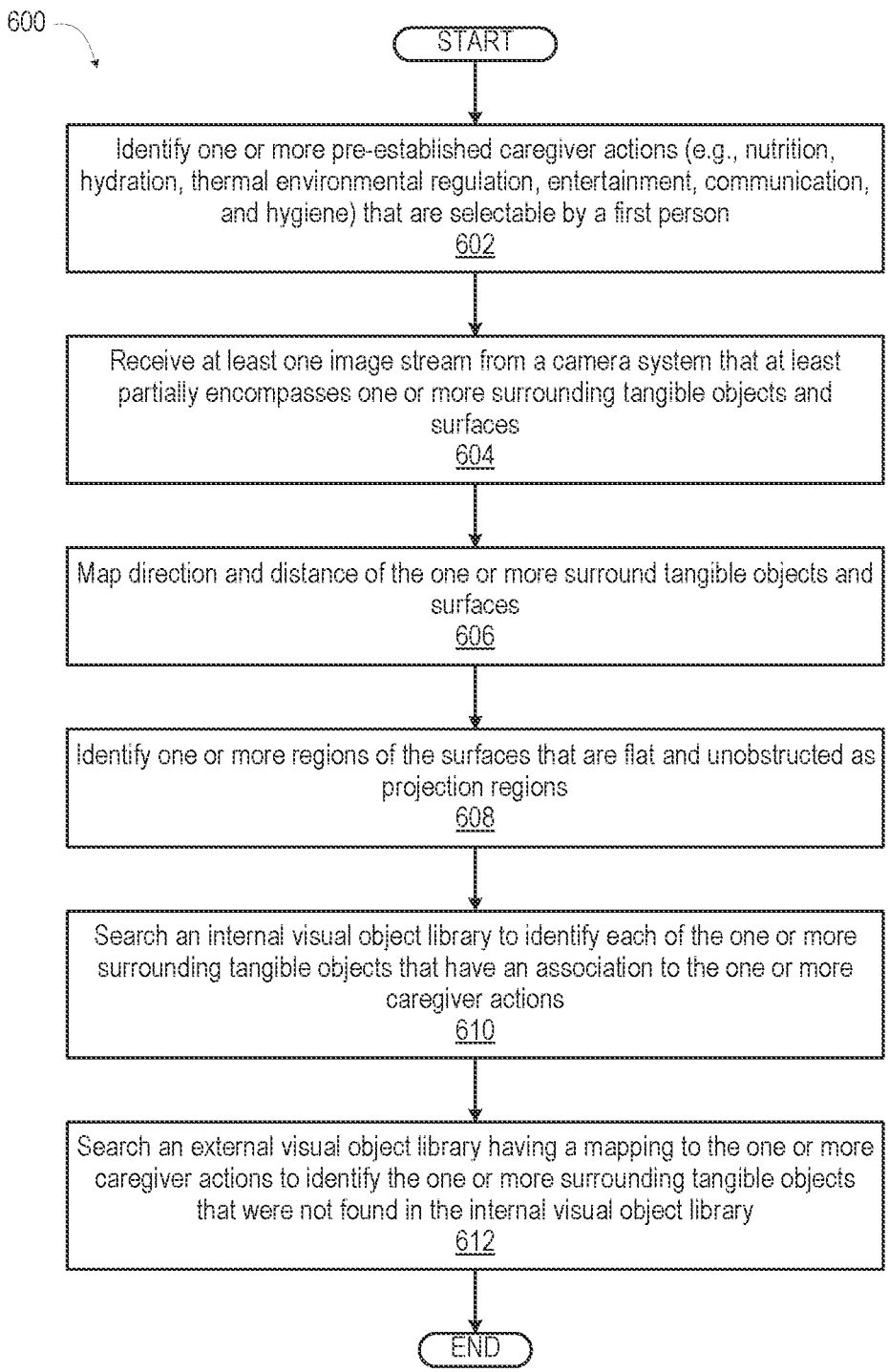
FIG. 6 presents a flow diagram of a method performed by the monitoring system of FIG. 5A for identifying associations of tangible objects with caregiver actions, according to one or more embodiments.
Figure 7:
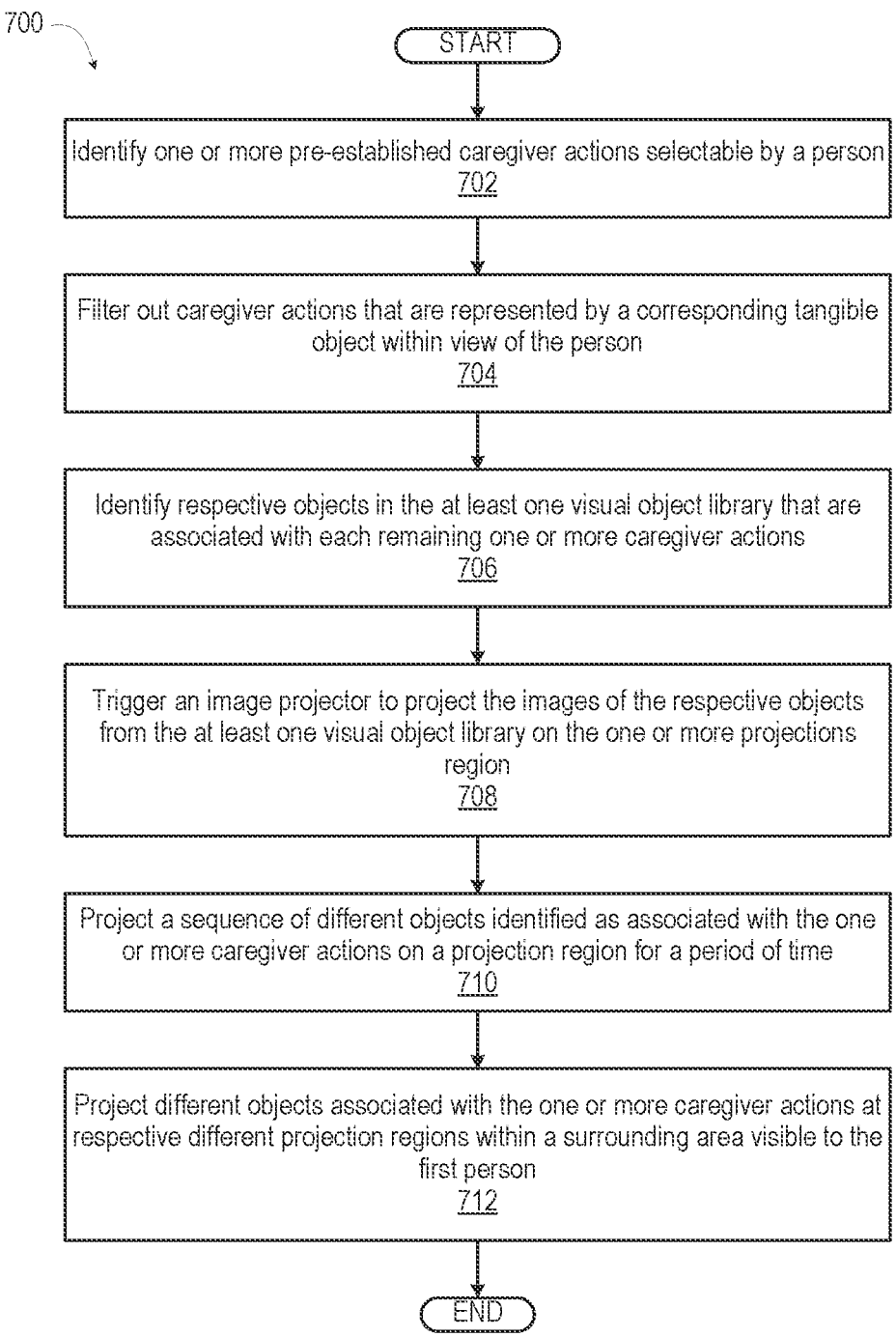
FIG. 7 presents a flow diagram of a method performed by the monitoring system of FIG. 5A for projecting objects with identified associations with caregiver actions on a surface viewable by a person with ambulatory and communication deficits or limitations, according to one or more embodiments.
Figure 8:
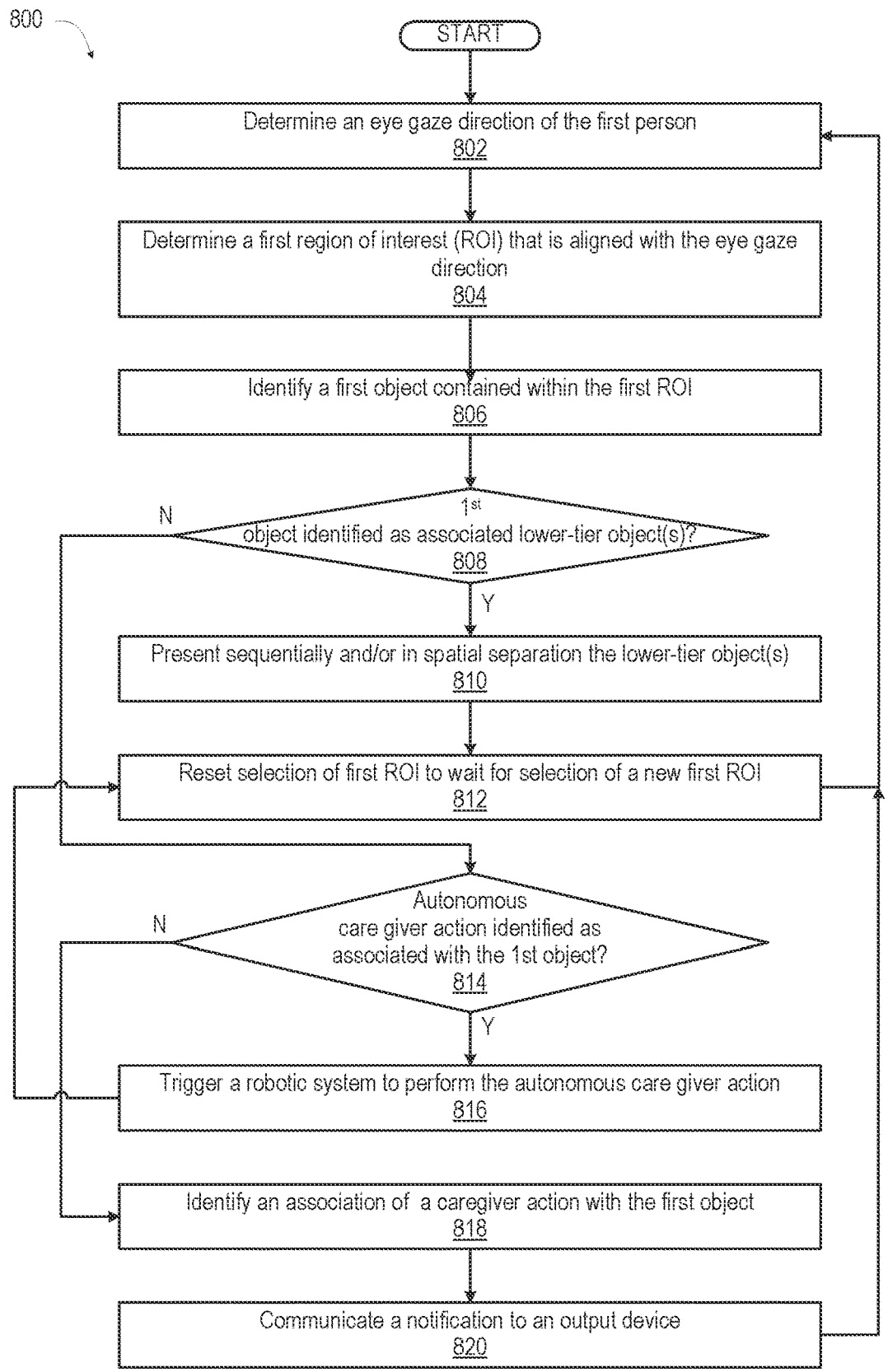
FIG. 8 presents a flow diagram of a method performed by the monitoring system of FIG. 5A for providing a contextual gaze-detection-based user selection for prompting caregiver actions by the person, according to one or more embodiments.

FIG. 6 presents a flow diagram of method 600 performed by a controller of a monitoring system for identifying associations of tangible objects with caregiver actions. FIG. 7 presents a flow diagram of method 700 performed by a controller of a monitoring system for projecting objects with identified associations with caregiver actions on a surface viewable by a person with ambulatory and communication deficits or limitations. FIG. 8 presents a flow diagram of method 800 performed by a controller of a monitoring system to provide a contextual gaze-detection-based user selection for prompting/requesting caregiver actions by the person. The descriptions of method 600 of FIG. 6, method 700 of FIG. 7, and method 800 of FIG. 8 are provided with general reference to the specific components illustrated within the preceding FIGS. 1-4 and 5A-5B and specific components referenced in methods 600 (FIG. 6), 700 (FIG. 7) and 800 (FIG. 8) may be identical or similar to components of the same name used in describing preceding FIGS. 1-4 and 5A-5B. In one or more embodiments, controller 102 (FIGS. 1-2) configures electronic device 101 (FIG. 1) or communication device (FIG. 2) to provide functionality of methods 600 (FIG. 6), 700 (FIG. 7) and 800 (FIG. 8).

With reference to FIG. 6, method 600 includes identifying one or more pre-established caregiver actions (e.g., nutrition, hydration, thermal environmental regulation, entertainment, communication, and hygiene) that are selectable by a first person (block 602). Method 600 includes receiving at least one image stream from a camera system that at least partially encompasses one or more surrounding tangible objects and surfaces (block 604). Method 600 includes mapping direction and distance of the one or more surround tangible objects and surfaces (block 606). Method 600 includes identifying one or more regions of the surfaces that are flat and unobstructed as projection regions (block 608). Method 600 includes searching an internal visual object library to identify each of the one or more surrounding tangible objects that have an association to the one or more caregiver actions (block 610). Method 600 includes searching an external visual object library having a mapping to the one or more caregiver actions to identify the one or more surrounding tangible objects that were not found in the internal visual object library (block 612). Then method 600 ends. In one or more embodiments, method 600 is periodically performed to capture changes in tangible objects positioned within view of the first person and to identify updates to predefined caregiver actions.

With reference to FIG. 7, method 700 includes identifying one or more pre-established caregiver actions selectable by a person (block 702). In one or more embodiments, method 700 includes filtering out caregiver actions that are represented by a corresponding tangible object within view of the person (block 704). Method 700 includes identifying respective objects in the at least one visual object library that are associated with each remaining one or more caregiver actions (block 706). Method 700 includes triggering an image projector to project the images of the respective objects from the at least one visual object library on the one or more projections region (block 708). The projection of the different images can be completed either serially (i.e., one at a time) or simultaneously. In one or more embodiments, method 700 includes projecting a sequence of different objects identified as associated with the one or more caregiver actions on a projection region for a period of time (block 710). In one or more embodiments, method 700 includes projecting different objects associated with the one or more caregiver actions at respective different projection regions within a surrounding area visible to the first person (block 712). Then method 700 ends.

With reference to FIG. 8, method 800 includes determining an eye gaze direction of the first person (block 802). Method 800 includes determining a first region of interest (ROI) that is aligned with the eye gaze direction (block 804). Method 800 includes identifying a first object contained within the first ROI (block 806). Method 800 includes determining whether the first object is identified as associated one or more lower-tier objects (decision block 808). In response to determining that the first object is identified as associated one or more lower-tier objects, method 800 includes presenting sequentially and/or in spatial separation the one or more lower-tier objects (block 810). Method 800 includes resetting selection of first ROI to wait for selection of a new first ROI (block 812). Then method 800 returns to block 802. In response to determining that the first object is not identified as associated one or more lower-tier objects in decision block 808, method 800 includes determining whether an autonomous caregiver action is identified as associated with the first object (decision block 814). In response to determining that an autonomous caregiver action is identified as associated with the first object, method 800 includes triggering a robotic system to perform the autonomous caregiver action (block 816). Then method 800 returns to block 812. In response to determining that an autonomous caregiver action is not identified as associated with the first object, method 800 includes identifying an association of a caregiver action with the first object (block 818). Method 800 includes communicating, using wired connection from a network interface or a wireless connection by a communication subsystem to an external network, a notification to an output device, which presents to a second person, an indication of interest by the first person in the caregiver action (block 820). Then method 800 returns to block 802.

Aspects of the present innovation are described above with reference to flowchart illustrations and/or block diagrams of methods, apparatus (systems) and computer program products according to embodiments of the innovation. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

As will be appreciated by one skilled in the art, embodiments of the present innovation may be embodied as a system, device, and/or method. Accordingly, embodiments of the present innovation may take the form of an entirely hardware embodiment or an embodiment combining software and hardware embodiments that may all generally be referred to herein as a "circuit," "module" or "system."

While the innovation has been described with reference to exemplary embodiments, it will be understood by those skilled in the art that various changes may be made, and equivalents may be substituted for elements thereof without departing from the scope of the innovation. In addition, many modifications may be made to adapt a particular system, device, or component thereof to the teachings of the innovation without departing from the essential scope thereof. Therefore, it is intended that the innovation is not limited to the particular embodiments disclosed for carrying out this innovation, but that the innovation will include all embodiments falling within the scope of the appended claims. Moreover, the use of the terms first, second, etc. do not denote any order or importance, but rather the terms first, second, etc. are used to distinguish one element from another.

The terminology used herein is for the purpose of describing particular embodiments only and is not intended to be limiting of the innovation. As used herein, the singular forms "a", "an" and "the" are intended to include the plural forms as well, unless the context clearly indicates otherwise. It will be further understood that the terms "comprise" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present innovation has been presented for purposes of illustration and description but is not intended to be exhaustive or limited to the innovation in the form disclosed. Many modifications and variations will be apparent to those of ordinary skill in the art without departing from the scope and spirit of the innovation. The embodiments were chosen and described in order to best explain the principles of the innovation and the practical application, and to enable others of ordinary skill in the art to understand the innovation for various embodiments with various modifications as are suited to the particular use contemplated.

What is claimed is:

1. A monitoring system comprising:
a camera system comprising at least one image capturing device and which captures a first image stream that encompasses eyes of a first person of interest and a second image stream that at least partially encompasses one or more surrounding objects and surfaces viewable by the first person;
a memory that stores an eye gaze detection monitoring (EGD) application;
a controller communicatively coupled to the camera system and the memory, and which:
executes the EGD application to determine an eye gaze direction of the first person;
determines a first region of interest (ROI) that is aligned with the eye gaze direction;
identifies a first object contained within the first ROI;
identifies an association of a caregiver action with the first object; and
communicates a notification to an output device, which presents to a second person, an indication of interest by the first person in the caregiver action.

2. The monitoring system of claim 1, wherein the caregiver action is associated with one of a group comprising: (i) nutrition; (ii) hydration; (iii) thermal environmental regulation; (iv) entertainment; (v) communication; and (vi) hygiene.

3. The monitoring system of claim 1, wherein the memory further comprises a visual object library, and the controller:
  recognizes, by referencing the visual object library, one or more objects, including the first object, present in the first ROI; and
  associates at least the first object with one more caregiver actions that are mapped within the visual object library.

4. The monitoring system of claim 3, further comprising a network interface that is communicatively connected via a network to an external visual object library, wherein the controller associates at least the first object with one more caregiver actions that are mapped within the external visual object library in response to not finding an association within the visual object library.

5. The monitoring system of claim 1, further comprising an image projector communicatively coupled to the controller, wherein the controller triggers the image projector to project the first image within the first ROI.

6. The monitoring system of claim 5, further comprising a memory that stores a visual object library that is communicatively coupled to the controller that:
  recognizes, using the visual object library, one or more tangible objects including the first object that are present in the at least one image stream in the at least one region;
  attempts to identify a respective tangible object of the one or more tangible objects associated with each of the one or more caregiver actions; and
  in response to determining that one or more caregiver actions are not represented by a respective tangible object recognized as present in the at least one image stream:
    identifies the first object in the visual object library that is associated with one of the caregiver actions; and
    triggers the image projector to project the first image on the first ROI.

7. The monitoring system of claim 5, wherein the controller projects a sequence of different objects associated with the one or more caregiver actions on the first ROI for a period of time.

8. The monitoring system of claim 5, wherein the controller projects different objects associated with the one or more caregiver actions at respective different regions within a surrounding area visible to the first person.

9. The monitoring system of claim 1, further comprising a communication subsystem that is communicatively coupled to the controller, wherein the controller wirelessly communicates a notification, using the communication subsystem, to a second communication device having the output device.

10. A method comprising:
  receiving at least one image stream from a camera system comprising at least one image capturing device and which captures a first image stream that encompasses eyes of a first person of interest and a second image stream that at least partially encompasses one or more surrounding objects and surfaces viewable by the first person;
  determining an eye gaze direction of the first person;
  determining a first region of interest (ROI) that is aligned with the eye gaze direction;
  identifying a first object contained within the first ROI;
  identifying an association of a caregiver action with the first object; and
  communicating a notification to an output device, which presents to a second person, an indication of interest by the first person in the caregiver action.

11. The method of claim 10, wherein the caregiver action is associated with one of a group comprising: (i) nutrition; (ii) hydration; (iii) thermal environmental regulation; (iv) entertainment; (v) communication; and (vi) hygiene.

12. The method of claim 10, further comprising:
  recognizing, by referencing a visual object library, one or more objects, including the first object, present in the first ROI; and
  associating at least the first object with one more caregiver actions that are mapped within the visual object library.

13. The method of claim 12, further comprising:
  communicatively connected, via a network interface and a network, to an external visual object library; and
  associating at least the first object with one more caregiver actions that are mapped within the external visual object library in response to not finding an association within the visual object library.

14. The method of claim 10, further comprising triggering an image projector to project the first image within the first ROI.

15. The method of claim 14, further comprising:
  recognizing, using a visual object library, one or more tangible objects in the at least one image stream including the first object that are present in the at least one region;
  attempting to identify a respective tangible object of the one or more tangible objects associated with each of the one or more caregiver actions; and
  in response to determining that one or more caregiver actions are not represented by a respective tangible object recognized as present in the at least one image stream:
    identifying the first object in the visual object library that is associated with one of the caregiver actions; and
    triggering the image projector to project the first image on the first ROI.

16. The method of claim 14, further comprising projecting a sequence of different objects associated with the one or more caregiver actions on the first ROI for a period of time.

17. The method of claim 14, further comprising projecting different objects associated with the one or more caregiver actions at respective different regions within a surrounding area visible to the first person.

18. The method of claim 10, further comprising wirelessly communicating the notification, using a communication subsystem, to a second communication device having an output device.

19. A computer program product comprising:
  a computer readable storage device; and
  program code on the computer readable storage device that when executed by a processor associated with a monitoring system, the program code enables the monitoring system to provide functionality of:
    receiving at least one image stream from a camera system comprising at least one image capturing device and which captures a first image stream that encompasses eyes of a first person of interest and a second image stream that at least partially encompasses one or more surrounding objects and surfaces viewable by the first person;
    determining an eye gaze direction of the first person;
    determining a first region of interest (ROI) that is aligned with the eye gaze direction;
    identifying a first object contained within the first ROI;

identifying an association of a caregiver action with the first object; and communicating a notification to an output device, which presents to a second person, an indication of interest by the first person in the caregiver action.

20. The computer program product of claim 19, wherein the program code enables the monitoring system to provide the functionality of:

recognizing, by referencing a visual object library, one or more objects, including the first object, present in the first ROI; and associating at least the first object with one more caregiver actions that are mapped within the visual object library, wherein the caregiver action is associated with one of a group comprising: (i) nutrition; (ii) hydration; (iii) thermal environmental regulation; (iv) entertainment; (v) communication; and (vi) hygiene.

* * * * *